United States Patent [19]

Hübsch et al.

[11] Patent Number: 5,976,772
[45] Date of Patent: *Nov. 2, 1999

[54] BLEACH-FIXING BATH FOR COLOR PHOTOGRAPHIC MATERIAL

[75] Inventors: Thomas Hübsch, Köln; Ralf Weimann, Leverkusen; Angelika Scholkmann, Leverkusen; Erika Spriewald, Leverkusen, all of Germany

[73] Assignee: Agfa Gevaert AG, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/940,715

[22] Filed: Sep. 30, 1997

[30] Foreign Application Priority Data

Oct. 10, 1996 [DE] Germany ............. 196 41 687

[51] Int. Cl.$^6$ ..................................... G03C 7/42
[52] U.S. Cl. ............................ 430/393; 430/460
[58] Field of Search ................... 430/460, 461, 430/393

[56] References Cited

U.S. PATENT DOCUMENTS

| | | | |
|---|---|---|---|
| 4,229,521 | 10/1980 | Frank et al. ............. | 430/372 |
| 4,444,873 | 4/1984 | Ishikawa et al. ......... | 430/393 |
| 4,963,474 | 10/1990 | Fujita et al. ............ | 430/393 |
| 5,093,228 | 3/1992 | Nakamura ................ | 430/460 |
| 5,352,568 | 10/1994 | Kuse et al. .............. | 430/461 |
| 5,453,348 | 9/1995 | Kuse et al. .............. | 430/461 |
| 5,695,915 | 12/1997 | Ueda et al. .............. | 430/393 |
| 5,814,439 | 9/1998 | Ishikawa ................ | 430/393 |

FOREIGN PATENT DOCUMENTS

| | | |
|---|---|---|
| 0 329 088 | 8/1989 | European Pat. Off. . |
| 0 330 048 | 8/1989 | European Pat. Off. . |

*Primary Examiner*—Hoa Van Le
*Attorney, Agent, or Firm*—Connolly, Bove, Lodge & Hutz, LLP

[57] ABSTRACT

A bleach/fixing bath, characterized in that it contains, apart from the active and auxiliary substances necessary for bleach/fixing, a phosphonocarboxylic acid having at least two carboxylic acid groups per molecule, is lower in odor and more stable than conventional bleaching baths.

6 Claims, No Drawings

BLEACH-FIXING BATH FOR COLOR PHOTOGRAPHIC MATERIAL

This invention relates to a process for processing colour photographic silver halide material using a low-odour bleach/fixing bath.

When photographic materials containing silver halide are processed, processing conventionally also includes bleaching and fixing or bleach/fixing stages. Iron complex salts of aminopolycarboxylic acids, for example the iron/ammonium complex of ethylenediaminetetraacetic acid (EDTA), are conventionally used to bleach the silver arising during photographic development. Acetic acid is generally used as the buffer in the bleaching or bleach/fixing bath. Disadvantages of using acetic acid include the volatility thereof, and the associated odour nuisance and health hazard.

This particularly applies in modern high speed processes which are characterised by high temperature processing and low replenishment rates, as both elevated bath temperatures and increasing concentrations of substances in the stated bath increase the odour problem. High speed processes are in turn preferentially used in so-called minilabs. These are often located directly in retail premises without any waste air extraction such that the odour escaping from the baths is troublesome not only to the operator but also to customers.

The stated processes with reduced replenishment rates moreover often result in the impairment of the minimum densities of the processed material (increase in $D_{min}$), probably due to the rising content of developer substance and salts. This particularly applies to water-saving processing variants (use of low-flow rinsing or stabilising bath).

If acetic acid is replaced by other buffer substances in order to overcome the stated odour problem, bleaching is often inhibited, i.e. the metallic silver present in the developed material is incompletely oxidised. This results in a distinct reduction in image quality and incomplete silver recycling, which is disadvantageous from both an environmental and an economic viewpoint.

Known alternatives to acetic acid are carboxylic acids containing more than one functional group in order to reduce volatility. These include, for example, maleic acid, succinic acid or adipic acid. While using maleic acid does indeed result in a distinct reduction in the odour nuisance, the above-stated inhibition of bleaching also occurs. A further disadvantage is the known light-induced isomerisation of maleic acid to fumaric acid as fumaric acid has lower solubility in water, so resulting in unwanted precipitates. A review of buffer substances which may be considered is given, for example, in EP-A-0 713 139 on pages 50 and 51.

It is also prior art to add an excess of free aminopolycarboxylic acid to the iron complex present in the bleaching or bleach/fixing bath (*Research Disclosure* 37038/1995, p. 108). However, completely replacing the acetic acid with an aminopolycarboxylic acid such as EDTA would be disadvantageous with regard to the environmental characteristics of the bath as most of the members of this class of substances can be biodegraded only with difficulty, if at all.

Instead of the above-stated excess of bleach complexing agent, it is also possible to add small quantities of other complexing agents to the bath. These are described, for example, in *Research Disclosure* 37038/1995, pp. 108–109. However, when used as buffer substances, they have the same disadvantageous characteristics as the bleach complexing agent. They may also reduce the bleaching action of the bath by recomplexing the iron.

Hydroxyethane-1,1-diphosphonic acid (HEDP) is often used as a complexing agent to prevent calcium or magnesium precipitation, especially in developer and stabilising baths. Since the bleaching or bleach/fixing baths of modern high speed processes are typically of an acidic to neutral pH, it is not usual to add HEDP to them. Using it as a buffer substance in such baths is, nonetheless, conceivable.

The use of phosphonocarboxylic acids has already been described for various photographic baths. DE-A-27 44 357, DE-A-27 34 655 and JP-N 54 096 026 thus describe tin complexes of this acid as a fogging agent in reversal processes.

DE-A-27 07 989, JP-N 55 067 747, U.S. Pat. No. 4,588,677, EP-A-0 285 010 and EP-A-0 325 278 confirm the suitability of phosphonocarboxlyic acids as anti-calcareous and heavy metal complexing agents in colour developers.

DE-A-34 12 857, DE-A-35 13 925, DE-A-35 22 622 and EP-A-0 283 174 disclose use as a heavy metal complexing agent in stabilising baths.

However, none of these disclosures gives any indication of an advantageous use in bleach/fixing baths. DE-A-27 32 153 and DE-A-32 48 359 describe the use inter alia of phosphonocarboxylic acids in a processing bath downstream from the bleaching bath, wherein bleaching is performed in the bleaching bath using iron salts, but not with iron complexes. The acids are intended to dissolve out any iron remaining in the material. No statement is made as to suitability in bleach/fixing baths already containing complexed iron.

In EP-A-0 329 088, certain bleach complexing agents are combined in bleaching baths with a plurality of buffer substances. However, only bleaching baths are disclosed. Other buffer substances are expressly proposed for the subsequent fixing or bleach/fixing bath (page 16, lines 16–19). Furthermore, the use of iron/EDTA is not provided by the invention and is described therein as disadvantageous.

The same applies to EP-A-330 043, in which the use of Fe/EDTA is likewise rejected. The pH range of the bleaching bath should be between 3.0 and 5.0. The bleaching bath is followed by a fixing or bleach/fixing bath which may contain inter alia a phosphonocarboxylic acid. It is, however, stated on page 39, lines 55–58 that combined use of bleaching complex and phosphonocarboxylic acid results in a considerable reduction in bleaching action. Consequently, the minimum value for bleaching and fixing is stated as 1 minute on page 40. Example 2 demonstrates that using iron/EDTA results in an elevated quantity of residual silver, i.e. in poor bleaching.

An object of the invention is accordingly to provide bleach/fixing baths for processing photographic materials which produce as little odour as possible. A further object is to provide corresponding bleaching baths having a bleaching action which equals or surpasses that achieved when acetic acid is used. The increase in minimum densities which often occurs in processes having low replenishment rates should also be prevented.

It is also intended to produce processing baths having elevated stability against microbial attack in the service state.

It has now surprisingly been found that the above-stated objects may be achieved by replacing acetic acid with specific phosphonic acids.

The present invention provides a process for processing an exposed colour photographic silver halide material comprising colour development and bleach/fixing treatment stages, characterised in that a bleach/fixing bath containing a nitrogen-free phosphonocarboxylic acid having at least 2 carboxylic acid groups is used for the bleach/fixing treatment stage.

Examples of suitable phosphonic acids are shown below:
P-1
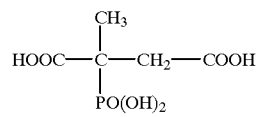
P-2
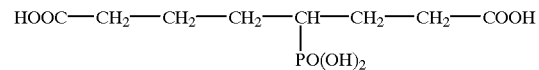
P-3
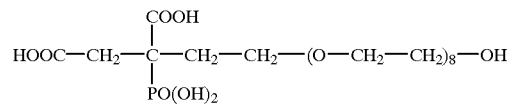
P-4
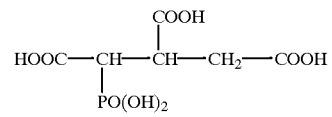
P-5
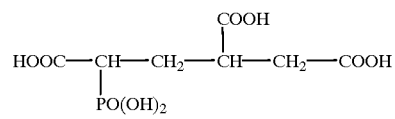
P-6
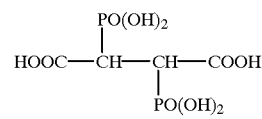
P-7
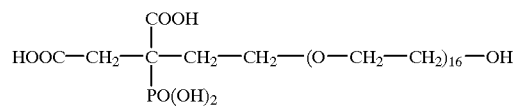
P-8
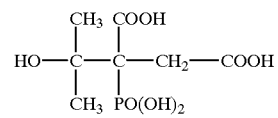
P-9
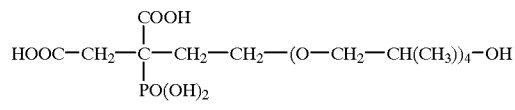
P-10
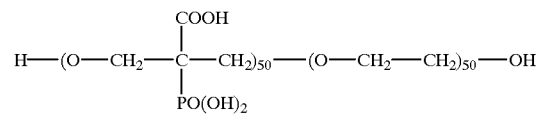
P-11
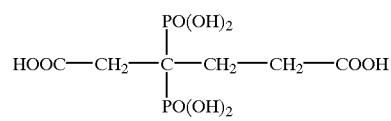
P-12
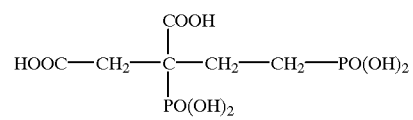
P-13
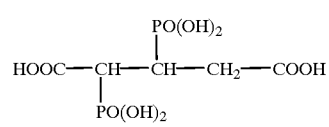
P-14
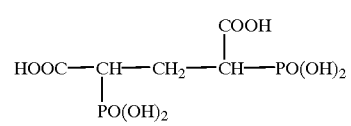
P-15
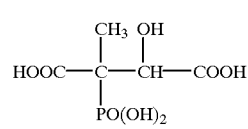
P-16
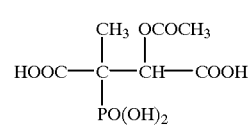
P-17
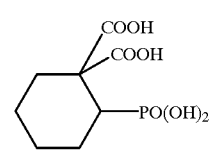
P-18
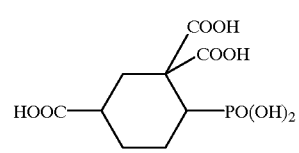

P-19
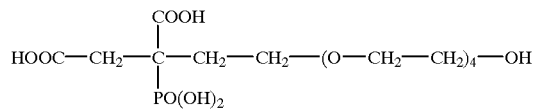
P-20
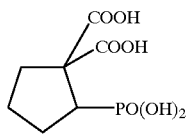
P-21
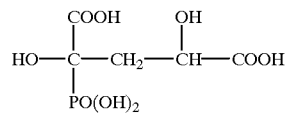
P-22
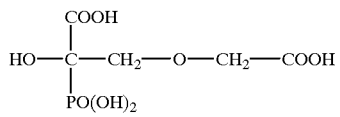
P-23
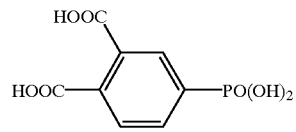
P-24
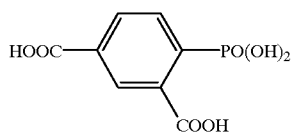
P-25
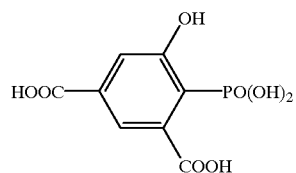
P-26
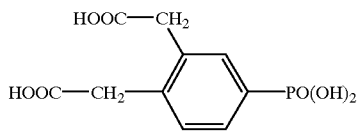
P-27
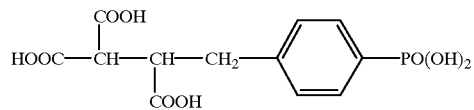
P-28
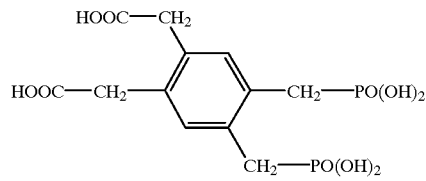
I-29
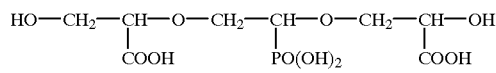
P-30
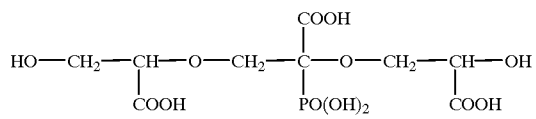
P-31
P-32

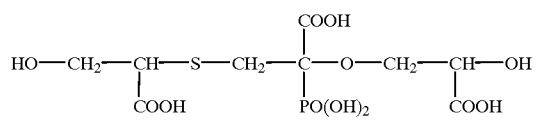
P-33
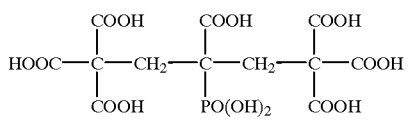
P-34
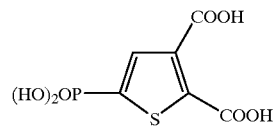
P-35
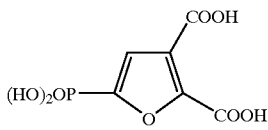
P-36
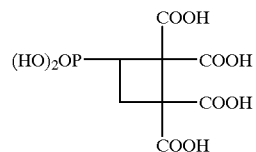
P-37
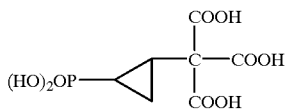
P-38
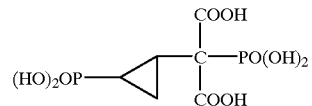
P-39
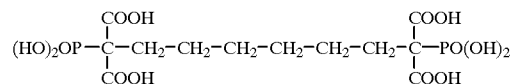
P-40
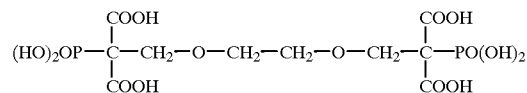
P-41
P-42
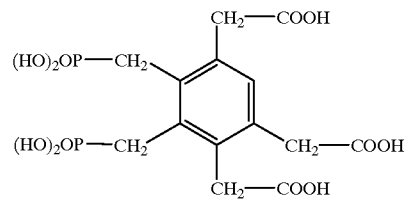
P-43
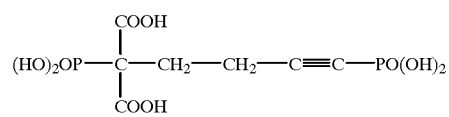
P-45
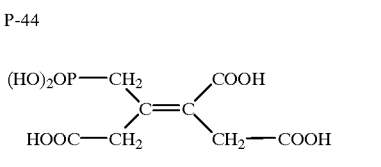
P-44
P-46

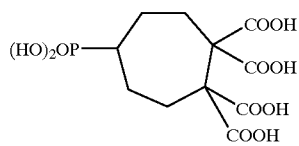
P-47
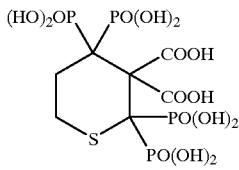
P-48
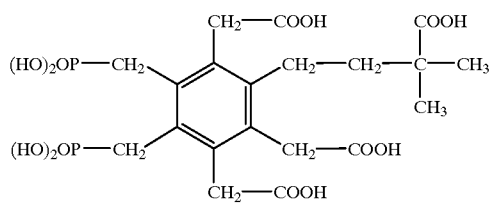
P-49
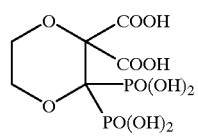
P-50
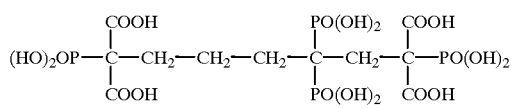
P-51
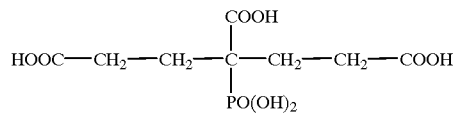
P-52
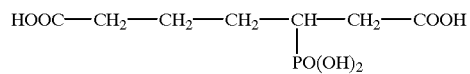
P-53
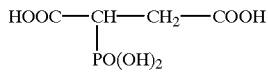
P-54
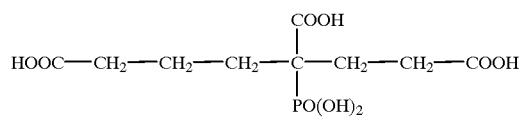
P-55
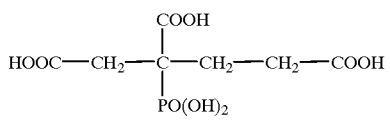
P-56
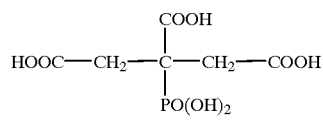
P-57
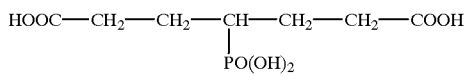
The bleach/fixing bath according to the invention preferably contains phosphonocarboxylic acids of the formula I:

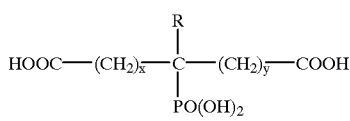

(I)

wherein
R means —H or —COOH,
x means 0, 1, 2 and
y means 1, 2, 3.

Examples of phosphonocarboxylic acids of the formula I are P-2 and P-51 to P-57.

The bleach/fixing bath according to the invention particularly preferably contains phosphonic acid P-54 (2-phosphono-1,2,4-butanetricarboxylic acid).

The phosphonic acids according to the invention are known and may be obtained by acid hydrolysis of the corresponding phosphonic acid dialkyl esters. A process for the production thereof is described in *Methoden der organischen Chemie,* Houben-Weyl, volume E2, *Organische Phosphor-Verbindungen II,* pp. 310 et seq., Georg Thieme Verlag, Stuttgart-New York 1982. DE-A-22 29 087 describes the synthesis of compound P-52, DE-A-27 45 982 and DE-A-38 29 961 describe the synthesis of compound P-54.

The phosphonocarboxylic acids are conventionally used in a concentration of 0.002 to 1.0 mol/l. In a preferred embodiment, the bleach/fixing bath according to the invention contains the phosphonocarboxylic acid in a quantity of 0.005–0.5 mol/l.

The bleach/fixing bath according to the invention is in particular suitable for processing colour photographic silver halide recording materials which contain on a reflective or transparent support (for example paper coated on both sides with polyethylene or cellulose triacetate film) at least one blue-sensitive, at least one green-sensitive and at least one red-sensitive silver halide emulsion layer, which are associated in the stated order with at least one yellow coupler, at least one magenta coupler and at least one cyan coupler.

The bleach/fixing bath according to the invention is in particular suitable for processing colour photographic silver halide materials, the silver halide content of which is at least 90 mol. % of silver chloride.

The bleach/fixing bath according to the invention is used within the conventional process for processing photographic silver halide materials. Details relating to the processing method and the chemicals required for this purpose are published together with example materials in EP-A-0 6 856 875, *Research Disclosure* 37 254, part 10 (1995), p. 294 and in *Research Disclosure* 37 038, parts XVI to XXIII (1995), pp. 95 et seq.

Iron complexes of organic acids may be used as bleaches. Apart from the stated EDTA, many other complexing agents are also suitable, such as propylenediaminetetraacetic acid (PDTA), nitrilotriacetic acid (NTA), diethylenetriaminetetraacetic acid (DTPA), alaninediacetic acid (ADA), N-acetamidoiminodiacetic acid together with the compounds stated on pp. 4–7 of EP-A-0 686 875. It is possible to use mixtures of the acids and/or the salts thereof, such as the sodium, potassium or ammonium salts.

Typical constituents of bleach/fixing baths are stated inter alia in EP-A-0 686 875, pp. 8–11 and in the literature cited therein.

It is particularly advantageous to combine the claimed, odour-reduced baths with other processing solutions which are also reduced in odour in comparison with the prior art. One substance which makes a substantial contribution towards odour nuisance is the antioxidant diethylhydroxylamine used in many colour developers. Derivatives of hydroxylamine or hydrazine, the volatility of which has been reduced by suitable substitution, may in general be used as a replacement. Examples of such compounds and other usable antioxidant substances and further important constituents are stated on pp. 12–25 of EP-A-0 686 875.

Ammonium-free bleaching baths are already advantageous on environmental grounds and, in conjunction with the substances according to the invention, the absence of ammonia with its strong odour is particularly favourable.

The processing process may be performed continuously with constant replenishment of the individual processing baths.

Replenishment may be performed, for example, by adding the necessary chemicals in solid form (tablets, pellets etc.), by apportioning concentrated solutions in two or more parts (direct replenishing) or also in the conventional manner by apportioning a single-component replenishing solution.

It is also possible to dispense with replenishment and to replace the tank contents, once spent, with fresh solution, as described inter alia in EP-A-0 701 167.

It is particularly advantageous to use the claimed bath compositions in apparatus having a low ratio of bath surface area to volume, as are stated, for example, in U.S. Pat. No. 5,436,118 and loc. cit.

EXAMPLE 1

Seven different bleach/fixing baths were prepared in accordance with the following: formulation:
Bleach/fixing bath
Ammonium thiosulphate (58 wt. %) 110.0 ml
Ammonia (25 wt. %) 2.7 ml
Sodium disulphite 16.2 g
Fe—NH$_4$—EDTA (48 wt. %) 101.0 ml
together with
  a) Acetic acid (85 wt. %) 7.7 ml
  b) P-52 (50 wt. %) 14.3 g
  c) P-54 (50 wt. %) 14.6 g
  d) P-58 (50 wt. %) 13.8 g
  e) Maleic acid 4.2 g
     Citric acid 3.5 g
  f) Sodium disulphite 15.0 g
  g) EDTA 7.9 g Once made up to 1000 ml, the pH value was, if necessary, adjusted to pH 5.85 with ammonia or phosphoric acid.

The solutions were heated to 38° C. in 2000 ml glass beakers and evaluated for odour by five test subjects. The ratings used were odourless, perceptible, troublesome, unpleasant and intolerable. The average results are shown in Table 1.

TABLE 1

| No. | Acid | Odour | Invention (I)/Comparison (C) |
|---|---|---|---|
| 1a | Acetic acid | unpleasant | C |
| 1b | P-52 | perceptible | I |
| 1c | P-54 | perceptible | I |
| 1d | P-57 | perceptible | I |
| 1e | Maleic/citric acid | perceptible | C |
| 1f | "Sulphurous acid" | troublesome | C |
| 1g | EDTA | perceptible | C |

Although a completely odourless bath was not obtained in any of the cases, replacing acetic acid with the acids according to the invention in every case brought about a distinct reduction in perceived odour. Test 1f shows that an elevated quantity of sulphite does not result in a substantial reduction in odour as the larger quantities of $SO_2$ released were found troublesome.

EXAMPLE 2

Baths 1a to 1g were titrated with potassium hydroxide solution in order to determine the buffering action thereof. Table 2 shows the results, with consumption being standardised to the quantity required for comparison tests, 2a. The bleach/fixing bath formulation described in Example 1 with 5.0 g of hydroxyethanediphosphonic acid (HEDP) as buffer was used in test 2h.

TABLE 2

| No. | Acid | Quantity of KOH [%] | Invention (I)/ Comparison (C) |
|---|---|---|---|
| 2a | acetic acid | 100 | C |
| 2b | P-52 | 105 | I |
| 2c | P-54 | 115 | I |
| 2d | P-57 | 130 | I |
| 2e | Maleic/citric acid | 90 | C |
| 2f | "Sulphurous acid" | 85 | C |
| 2g | EDTA | 90 | C |
| 2h | HEDP | 85 | C |

The acids according to the invention exhibit an extraordinarily good buffer action, superior to that of acetic acid. In contrast, baths 2e, 2f, 2g and 2h exhibit an inadequate action.

EXAMPLE 3

A multi-layer colour photographic recording material was produced by applying the following layers in the stated sequence onto a film support made from paper coated on both sides with polyethylene. All quantities are stated per 1 $m^2$; the quantity of silver is stated as $AgNO_3$:

Layer 1 (Substrate layer)
    0.10 g of gelatine
Layer 2 (Blue-sensitive layer):
    Blue-sensitive silver halide emulsion (99.5 mol. % chloride, 0.5 mol. % bromide, average grain diameter 0.9 μm) prepared from 0.50 g of $AgNO_3$, containing
    1.25 g of gelatine
    0.42 g of yellow coupler Y-1
    0.18 g of yellow coupler Y-2
    0.50 g of tricresyl phosphate (TCP)
    0.10 g of stabiliser ST-1
    0.70 mg of blue sensitiser S-1
    0.30 mg of stabiliser ST-2
Layer 3 (Interlayer)
    1.10 g of gelatine
    0.06 g of oxform scavenger SC-1
    0.06 g of oxform scavenger SC-2
    0.12 g of TCP
Layer 4 (Green-sensitive layer)
    Green-sensitive silver halide emulsion (99.5 mol. % chloride, 0.5 mol. % bromide, average grain diameter 0.47 μm) prepared from 0.40 g of $AgNO_3$, containing
    0.77 g of gelatine
    0.21 g of magenta coupler M-1
    0.15 g of magenta coupler M-2
    0.05 g of magenta coupler M-3
    0.06 g of stabiliser ST-3
    0.12 g of oxform scavenger SC-2
    0.34 g of dibutyl phthalate (DBP)
    0.70 mg of green sensitiser S-2
    0.50 mg of stabiliser ST-4
Layer 5 (UV protective layer)
    1.15 g of gelatine
    0.50 g of UV absorber UV-1
    0.10 g of UV absorber UV-2
    0.03 g of oxform scavenger SC-1
    0.03 g of oxform scavenger SC-2
    0.35 g of TCP
Layer 6 (Red-sensitive layer)
    Red-sensitive silver halide emulsion (99.5 mol. % chloride, 0.5 mol. % bromide, average grain diameter 0.5 μm) prepared from 0.30 g of $AgNO_3$, containing
    1.0 g of gelatine
    0.40 g of cyan coupler C-1
    0.05 g of cyan coupler C-2
    0.46 g of TCP
    0.03 mg of red sensitiser S-3
    0.60 mg of stabiliser ST-5
Layer 7 (UV protective layer)
    0.35 g of gelatine
    0.15 g of UV absorber UV-1
    0.03 g of UV absorber UV-2
    0.09 g of TCP
Layer 8 (Protective layer)
    0.90 g of gelatine
    0.05 g of optical brightener W-1
    0.07 g of mordant (PVP)
    1.20 mg of silicone oil
    2.50 mg of spacers (polymethyl methacrylate, average particle size 0.8 μm)
    0.30 g of hardener H-1
Compounds used in Example 3:

Y-1

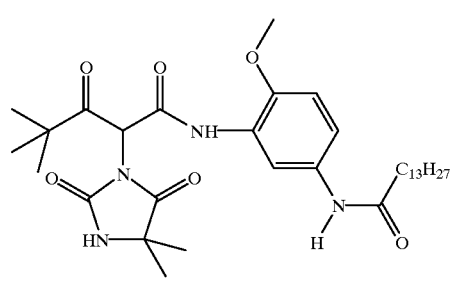

Y-2
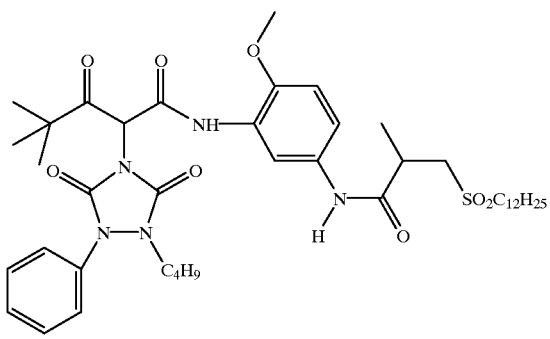
M-1
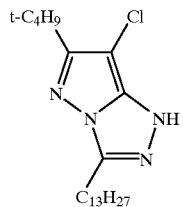
M-2
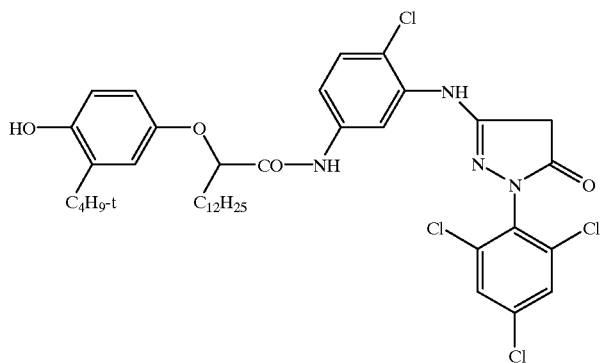
M-3
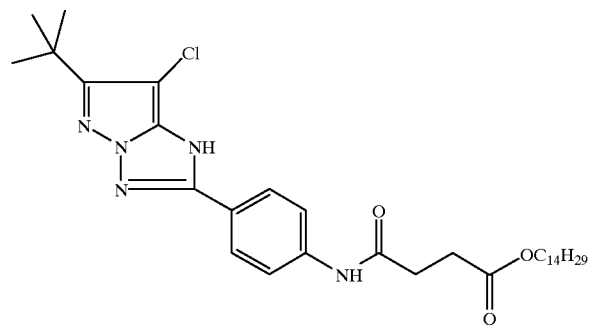
C-1
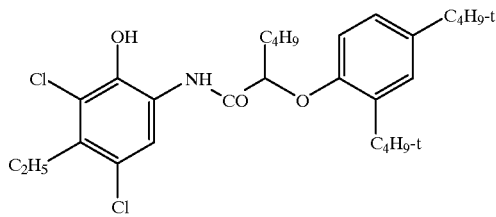

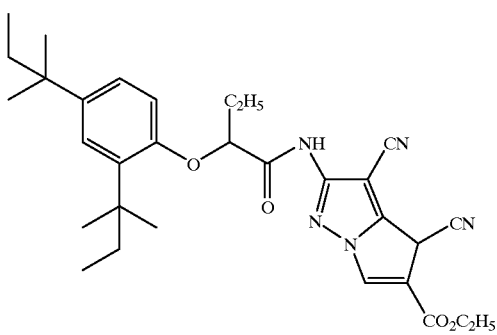
C-2
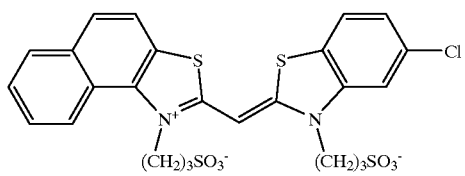
S-1
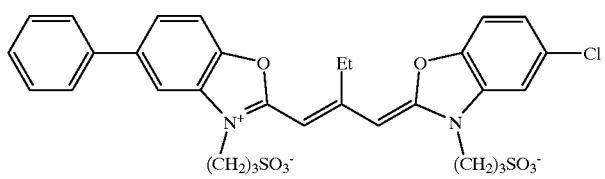
S-2
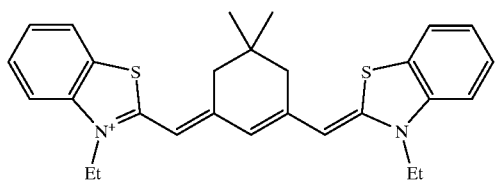
S-3
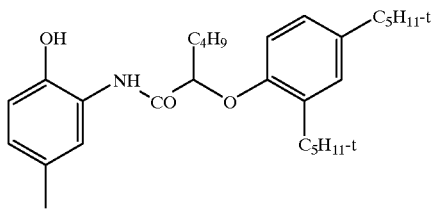
ST-1
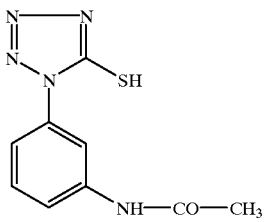
ST-2

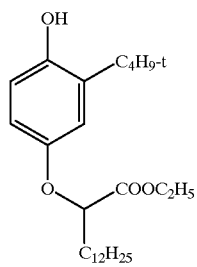
ST-3
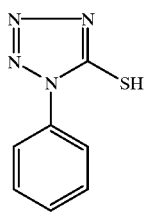
ST-4
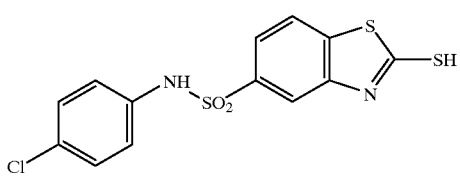
ST-5
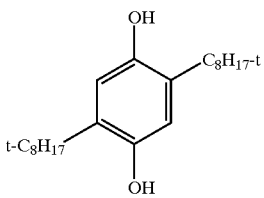
SC-1
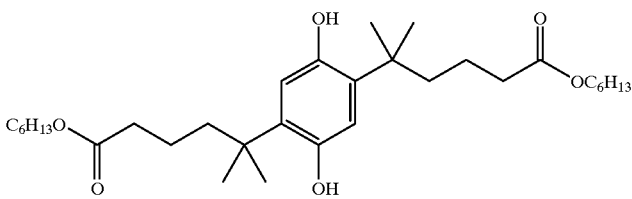
SC-2
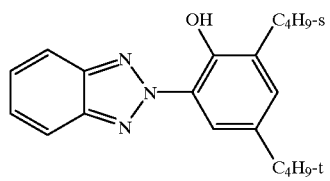
UV-1
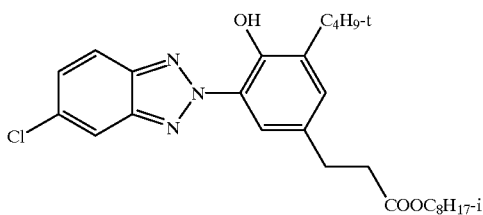
UV-2

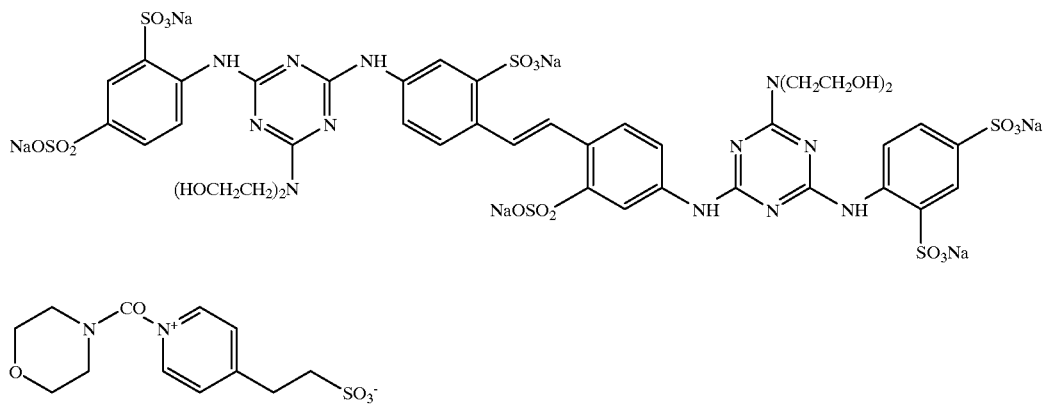

The colour photographic recording material is exposed through a step wedge. During exposure, additional filters are placed in the beam path of the exposure unit such that the wedge appears neutral at an optical density of D=0.6. The exposed material is processed using the following method:

| Stage | Time | Temperature |
|---|---|---|
| Development | 45 s | 35° C. |
| Bleach/fixing | 45 s | 35° C. |
| Stabilising bath | 90 s | 33° C. |

In order to simulate a bleach/fixing bath at a state of equilibrium, 1600 ml of each of solutions a–g from Example 1 were combined with 400 ml of developer over-flow and 4 g of silver nitrate. One strip of the material exposed as described above was manually processed with exclusion of light in the solutions which had been heated to 35° C.

The other processing baths were prepared in accordance with the following instructions:

Colour developer solution

Tetraethylene glycol 20.0 g
N,N-diethylhydroxylamine 4.0 g
(N-ethyl-N-(2-methanesulphonamido)ethyl)-4-amino-3-methyl-benzene sulphate 5.0 g
Potassium sulphite 0.2 g
Potassium carbonate 30.0 g
Polymaleic anhydride 2.5 g
Hydroxyethanediphosphonic acid 0.2 g
Optical brightener (4,4'-diaminostilbene type) 2.0 g
Potassium bromide 20 mg
make up to 1000 ml with water, adjust pH value to pH=10.2 with KOH or $H_2SO_4$.

Stabilising bath

Water 900 ml
Sodium disulphite 2 g
Hydroxyethanediphosphonic acid, disodium salt 4 g
Sodium benzoate 0.5 g
make up to 1000 ml with water.

The bleaching time in the bleach/fixing bath was determined using IR goggles, i.e. the time until no silver was any longer visible using the IR goggles. Table 3 shows the results.

TABLE 3

| No. | Acid | Bleaching time [s] | Invention (I)/ Comparison (C) |
|---|---|---|---|
| 3a | Acetic acid | 30 | C |
| 3b | P-52 | 27 | I |
| 3c | P-54 | 26 | I |
| 3d | P-57 | 27 | I |
| 3e | Maleic/citric acid | 37 | C |
| 3f | "Sulphurous acid" | 31 | C |
| 3g | EDTA | 28 | C |

It is clear that the acids according to the invention inhibit silver bleaching the least.

EXAMPLE 4

The material described in Example 3 was processed with bleach/fixing baths a–g which had been made up to a state of equilibrium under the conditions stated in Example 3. The specimens were then stored for 1 week at 60° C., 90% relative atmospheric humidity and the increase in minimum density $\Delta D_{min}$ determined. Table 4 shows the results.

TABLE 4

| No. | Acid | $\Delta D_{min}$ | Invention (I)/Comparison (C) |
|---|---|---|---|
| 4a | Acetic acid | 0.12 | C |
| 4b | P-52 | 0.07 | I |
| 4c | P-54 | 0.09 | I |
| 4d | P-57 | 0.07 | I |
| 4e | Maleic/citric acid | 0.10 | C |
| 4f | "Sulphurous acid" | 0.22 | C |
| 4g | EDTA | 0.21 | C |

Addition of the acids according to the invention brings about a significant improvement in the storage stability of the processed material.

We claim:

1. A process for processing an exposed color photographic silver halide material comprising color development and bleach/fixing treatment stages wherein said color development and bleach/fixing treatment stages consist of a two stage process with the first stage being said color development and the second stage being said bleach/fixing treatment and wherein, a bleach/fixing bath containing a nitrogen-free phosphonocarboxylic acid having at least 2 carboxylic acid groups is used for the bleach/fixing treatment stage.

2. The process for processing according to claim 1, wherein the phosphonocarboxylic acid is of the formula I

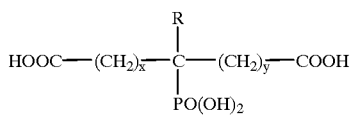
(I)

in which

R is H or —COOH;
x is 0 (zero), 1 or 2; and
y is 1, 2 or 3.

3. The process according to claim 2, wherein the phosphonocarboxylic acid is 2-phosphono-1,2,4-butanetricarboxylic acid.

4. The process according to claim 1, wherein the bleach/fixing bath contains an iron(III) complex of ethylenediaminetetraacetic acid as the bleach and substantially no acetic acid.

5. The process according to claim 1, wherein the duration of treatment with the bleach/fixing bath is no more than 45 seconds.

6. The process according to claim 3, wherein the bath contains the phosphonocarboxylic acid in the concentration of 0.005 to 0.5 mol/l.

* * * * *